United States Patent
Crawford et al.

(10) Patent No.: US 11,227,507 B2
(45) Date of Patent: Jan. 18, 2022

(54) WEARABLE TECHNOLOGY EMPLOYED IN INJURY DETECTION, PREVENTION AND SKILLS TRAINING

(71) Applicant: INTERNATIONAL BUSINESS MACHINES CORPORATION, Armonk, NY (US)

(72) Inventors: Glenn Crawford, Cary, NC (US); Adam Bishop, Raleigh, NC (US); Christopher Florence, Cary, NC (US); Rocky McMahan, Wake, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 615 days.

(21) Appl. No.: 16/157,706

(22) Filed: Oct. 11, 2018

(65) Prior Publication Data

US 2020/0118459 A1 Apr. 16, 2020

(51) Int. Cl.
| | |
|---|---|
| G09B 19/00 | (2006.01) |
| G16H 20/30 | (2018.01) |
| G16H 40/63 | (2018.01) |
| G06F 1/16 | (2006.01) |

(52) U.S. Cl.
CPC .......... G09B 19/003 (2013.01); G06F 1/163 (2013.01); G16H 20/30 (2018.01); G16H 40/63 (2018.01)

(58) Field of Classification Search
CPC ...... G09B 19/003; G16H 20/30; G16H 40/63; G06F 1/163
See application file for complete search history.

(56) References Cited

U.S. PATENT DOCUMENTS

| | | | |
|---|---|---|---|
| 8,025,632 B2 | 9/2011 | Einarsson | |
| 8,109,858 B2 | 2/2012 | Redmann | |
| 8,821,305 B2 * | 9/2014 | Cusey | A63B 24/0062 473/207 |
| 2009/0023122 A1 * | 1/2009 | Lieberman | G16H 20/70 434/258 |

(Continued)

FOREIGN PATENT DOCUMENTS

WO WO2015139089 A1 9/2015

OTHER PUBLICATIONS

Mell, Peter and Tim Grance, "The NIST Definition of Cloud Computing," National Institute of Standards and Technology, Information Technology Laboratory, Special Publication 800-145, Sep. 2011, pp. 1-7.

(Continued)

*Primary Examiner* — Mohamed Barakat
*Assistant Examiner* — Rufus C Point
(74) *Attorney, Agent, or Firm* — Terri Maranzano, Esq.; Kevin P. Radigan, Esq.; Heslin Rothenberg Farley & Mesiti P.C.

(57) ABSTRACT

Data regarding a movement being performed by a subject during an activity is obtained from wearable apparel, having one or more sensors, worn by the subject. Based at least in part on the data obtained by the wearable apparel, it is automatically detected that the movement has a potential of causing injury to the subject. Based on automatically detecting that the motion has the potential of causing injury to the subject, application of one or more physical stimuli is initiated to cause the subject to adjust the movement to prevent the injury.

18 Claims, 10 Drawing Sheets

(56) References Cited

U.S. PATENT DOCUMENTS

| | | | |
|---|---|---|---|
| 2009/0024062 A1* | 1/2009 | Einarsson | A61F 5/01 600/595 |
| 2012/0143093 A1* | 6/2012 | Stirling | A63B 69/3623 600/592 |
| 2012/0322570 A1* | 12/2012 | Allen | A61B 5/1122 473/266 |
| 2014/0135593 A1 | 5/2014 | Jayalth et al. | |
| 2015/0022362 A1 | 1/2015 | Lucas et al. | |
| 2017/0156662 A1* | 6/2017 | Goodall | A61B 5/0036 |
| 2017/0164876 A1* | 6/2017 | Hyde | A61B 5/389 |
| 2017/0251972 A1* | 9/2017 | Jayaraman | A61B 5/6806 |
| 2017/0291086 A1* | 10/2017 | Lee | G06F 3/011 |
| 2018/0116854 A1 | 5/2018 | Guerrier | |
| 2019/0000350 A1* | 1/2019 | Narayan | A61B 5/0826 |
| 2019/0009133 A1* | 1/2019 | Mettler May | A63B 24/0075 |
| 2020/0268287 A1* | 8/2020 | Discenzo | A61B 5/6831 |
| 2020/0391078 A1* | 12/2020 | Cusey | A61B 5/6804 |

OTHER PUBLICATIONS

Rawashdeh, Samir A. et al., "Wearable Motion Capture Unit for Shoulder Injury Prevention," IEEE 12$^{th}$ International Conference on Wearable and Implantable Body Sensor Networks, May 2015, pp. 1-6.

Yurtman, Aras et al., "Automated Evaluation of Physical Therapy Exercises Using Multi-Template Dynamic Time Warping on Wearable Sensor Signals," Computer Methods and Programs in Biomedicine 117, Jul. 2014, pp. 189-207.

\* cited by examiner

WEARABLE TECHNOLOGY EMPLOYED IN INJURY DETECTION, PREVENTION AND SKILLS TRAINING

BACKGROUND

One or more aspects relate, in general, to wearable technology, and in particular, to employing wearable technology in detecting and preventing potential injuries, as well as in performing skills training.

Individuals participate in many activities in which injuries may occur. These activities include various sports or other activities including, for instance, weight lifting, dance, yoga, soccer, baseball, running, football, skiing, tennis, rehabilitation, etc. An individual may perform a skill associated with an activity in such a way that it may cause injury. Further, an individual may perform a skill incorrectly in which performance is impaired.

SUMMARY

Shortcomings of the prior art are overcome and additional advantages are provided through the provision of a method of facilitating prevention of injury. The method includes obtaining, via a processor, data regarding a movement being performed by a subject during an activity. The data is obtained from wearable apparel worn by the subject, and the wearable apparel has one or more sensors. Based at least in part on the data obtained by the wearable apparel, it is automatically detected that the movement has a potential of causing injury to the subject. Based on automatically detecting that the movement has the potential of causing injury to the subject, application of one or more physical stimuli is initiated to cause the subject to adjust the movement to prevent the injury.

Systems and computer program products relating to one or more aspects are also described and claimed herein. Further, services relating to one or more aspects are also described and may be claimed herein.

Additional features and advantages are realized through the techniques described herein. Other embodiments and aspects are described in detail herein and are considered a part of the claimed aspects.

BRIEF DESCRIPTION OF THE DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

DETAILED DESCRIPTION

Figure 1A:
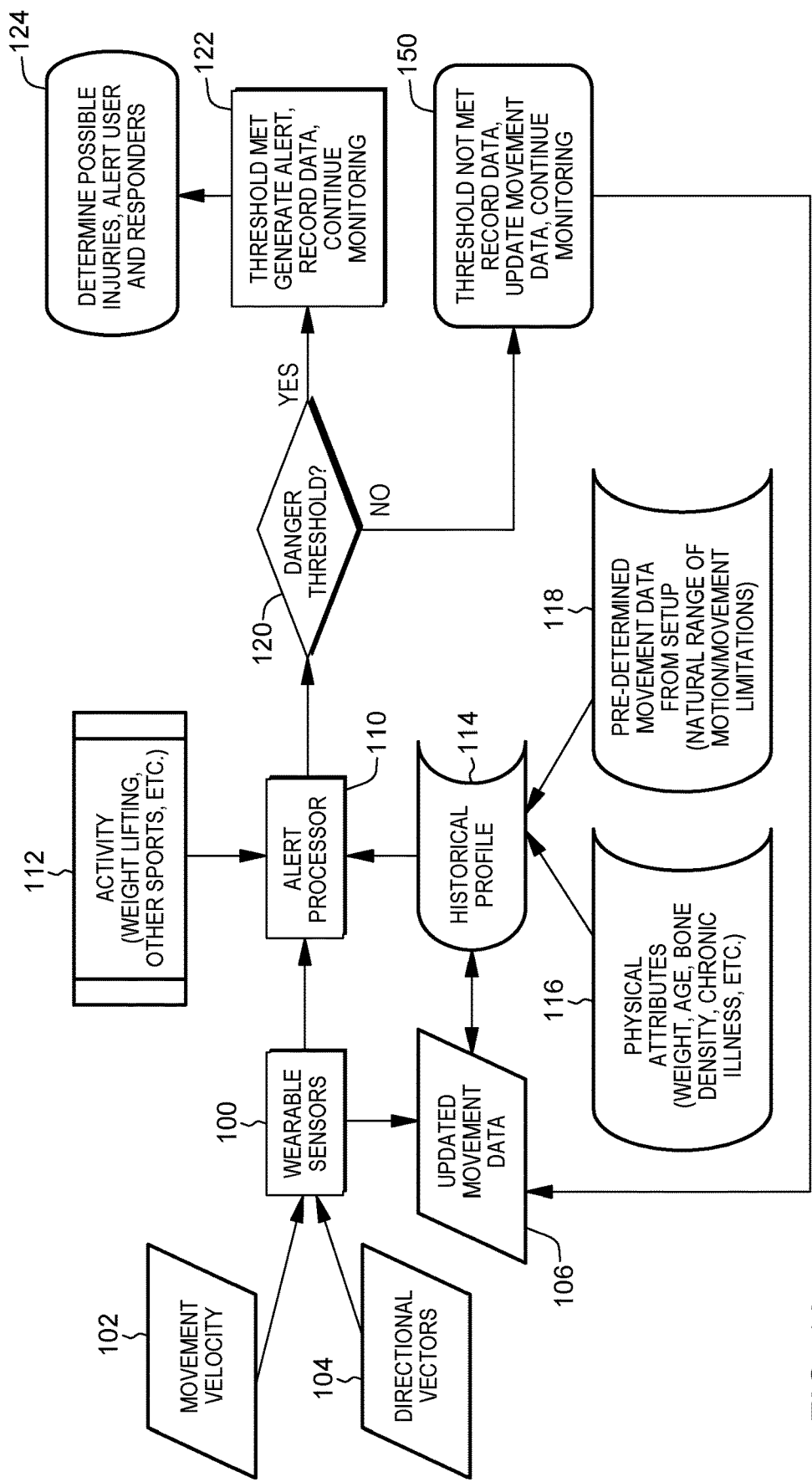
FIG. 1A depicts one example of alert processing to be used in, e.g., detecting and/or preventing injuries, in accordance with one or more aspects of the present invention.

In accordance with one or more aspects, detection of potential injuries and/or prevention of such injuries during participation in select activities is provided. The select activities include sports or other activities, such as weight lifting, dance, yoga, soccer, baseball, running, football, tennis, skiing, rehabilitation, etc. Many activities may be selected, and the activities described herein are just examples, and not meant to be limiting in any way.

In participating in an activity, a subject performs particular skills of the activity or moves in certain ways. To detect that a particular movement or performance of a particular skill may cause injury to the subject performing that movement or skill, wearable technology, cognitive technology and/or machine learning are employed. Further, based on detection of potential injury, the wearable technology, cognitive technology and/or machine learning are used, in one aspect, to prevent the injury. Moreover, in one or more aspects, the wearable technology, cognitive technology and/or machine learning are used in skills training. As examples, the subject may be human or non-human, such as, for instance, a person, an animal, a robot, a moveable structure, etc.

In one aspect, the detection of the potential injury is individualistic in that it considers the characteristics, limitations and/or restrictions of a particular subject (also referred to herein as an individual). In one embodiment, the range of motion for a particular subject depends on certain factors, including, but not limited to, age, injury, health, physical limitations or restrictions, etc. Also, in one aspect, the particular activity being performed is taken into consideration in detecting and/or preventing an injury or in skills training. Since different activities have unique movements and potential dangers, different sensory settings or modes are defined, in one example, for the different activities. As an example, a subject that is elderly or in poor physical condition may have more conservative settings than a professional athlete. Therefore, in one embodiment, to assist in creating settings for a subject, the subject goes through a series of movements during a setup phase. The sensors that are on, within or otherwise associated with a wearable apparel (e.g., a brace, wrap, shirt, pants, socks, eyewear, headband, caps, wristband, jacket, watch, jewelry, trackers, etc.) record the current range of movement for the subject and use that data to help determine normal movement limitations and to adjust the settings accordingly.

A history of the data is maintained, in one aspect, and used to dynamically adjust settings based on historical trends. Different external influences could also be input, such as use of a walker, cane, crutches, a wheelchair or other assistance device.

If the detected movement of the individual goes beyond the normal range for the particular individual, the movement is analyzed for possible injury. Further, if a certain threshold is met, an alert may be provided. Yet further, a different alert may be provided if injury, as opposed to potential injury, is detected. For example, if a recorded leg movement is only possible if the leg was broken, then an additional alert notification is generated. This notification is sent, in one or more aspects, to other individuals (e.g., one or more selected by the subject, a paramedic, 911, a doctor, etc.) via one or more mechanisms, such as text, email, phone call, audible message, etc. The recorded movement leading up to and including the injury is automatically saved, in one embodiment, for future viewing. This recording could be used by others, such as first responders, doctors, lawyers, trainers, coaches, etc. to help piece together the events leading up to and during the event causing injury.

One embodiment of alert processing to be used in detecting a potential injury and taking action based thereon is described with reference to FIG. 1A. Referring to FIG. 1A, in one example, one or more sensors 100 of a wearable apparel (referred to herein as wearable sensors) track different statistics, including, for instance, movement velocity 102 and directional vectors 104 of various limbs or body parts, depending on placement of the sensors. As examples, the sensors include accelerometer sensors, electromyographic sensors, gyroscopic sensors (e.g., to track angular velocity) and/or other sensors now known or later developed used in providing various statistics relating to performing a movement. The sensors are manufactured, for instance, as devices, such as chips or other processing devices, fibers, and/or other types. One or more sensors are included on, within and/or associated with a wearable apparel. As indicated herein, there are many types of wearable apparel, including, but not limited to, a brace, wrap, shirt, pants, socks, eyewear, headband, caps, wristband, jacket, watch, jewelry, trackers, etc. Although examples of sensors and wearable apparel are provided herein, these are just examples and not meant to be limiting in any way. Other sensors and/or wearable apparel may be used without departing from one or more aspects of the present invention.

Figure 3B:
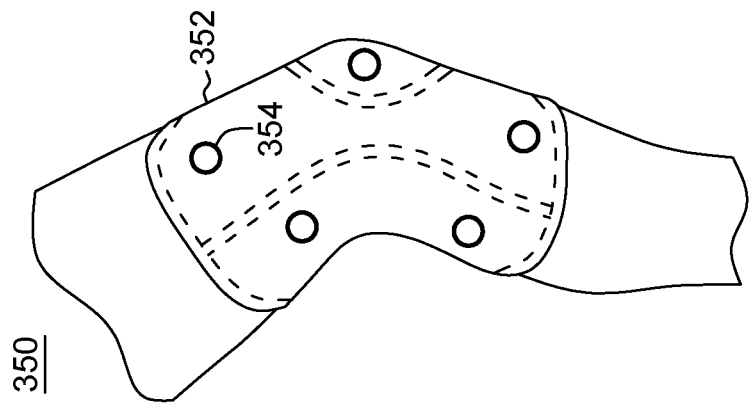
FIGS. 3A-3B depict examples of subjects wearing apparel with sensors used to detect/prevent injury and/or to facilitate skills training, in accordance with one or more aspects of the present invention.
Figure 3A:
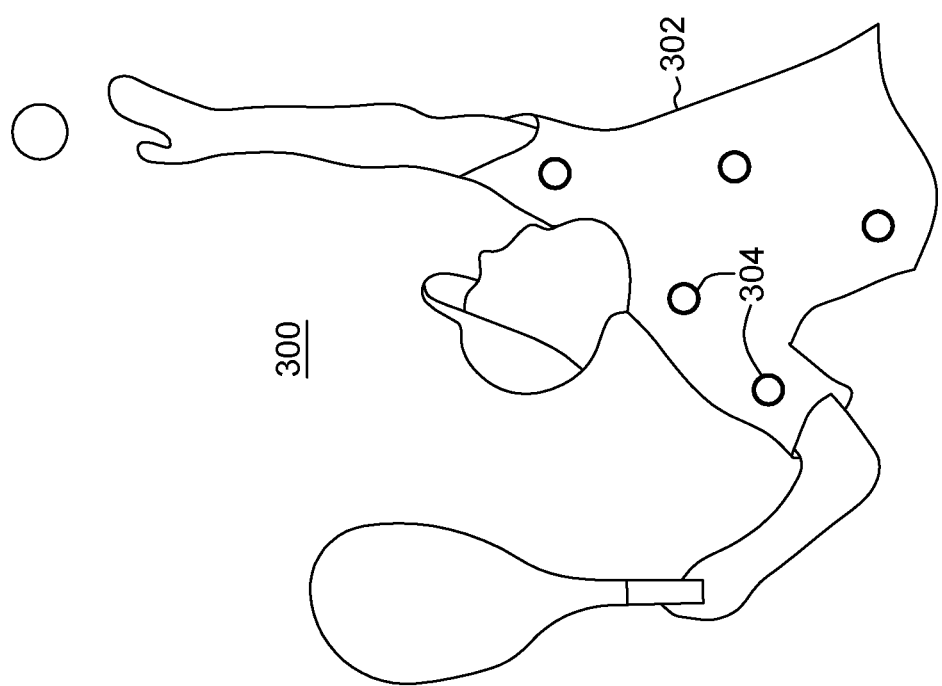

As a specific example, one or more sensors may be situated in a wearable apparel, such as, but not limited to, a brace, shirt or other apparel worn over the shoulder that monitors direction and/or velocity in movement of the shoulder in various motions, such as throwing overhand or underhand, picking up an item, weight lifting, etc. For example, as shown in FIG. 3A, a subject, such as a person 300, is wearing a wearable apparel, such as a shirt 302, that includes a plurality of sensors 304. One or more of the sensors may be used to determine whether a motion performed by the shoulder, arm and/or other body part being sensed may cause injury when participating in a particular activity, such as tennis. In this example, there are sensors in a number of positions of the shirt; however, in other examples, there may be less or more sensors; there may be sensors in different positions; and/or there may be more or less sensors in a specific position. Further, in another example, more than one wearable apparel may be used to monitor other body parts or areas and used to detect potential injury and/or prevent injury.

Similarly, one or more sensors may be situated in a wearable apparel, such as, but not limited to, a brace, wrap, pants or other apparel for the knee or leg that monitors direction and/or velocity in movement of the knee or leg in various motions, such as kicking, bending, lifting, etc. For example, as shown in FIG. 3B, a subject, such as a person, is wearing a wearable apparel, such as a knee brace 352, over a body part of the subject, such as a portion of a leg 350 that includes the knee. Knee brace 352 includes a plurality of sensors 354, and one or more of the sensors are used, in accordance with an aspect of the present invention, to determine whether a motion performed by the knee and/or a part of the leg being sensed may cause injury. In this example, there are sensors in a number of positions of the brace; however, in other examples, there may be less or more sensors; there may be sensors in different positions; and/or there may be more or less sensors in a specific position.

Based on obtaining data from the sensors, updated movement data 106 is updated with the sensed data and/or the data is provided as input to a processor 110. The processor is used, in one example, to provide alerts, and therefore, is referred to herein as an alert processor.

Processor 110 also receives as input activity information 112 and/or historical profile information 114. Activity information 112 includes, for instance, movement data for specific activities, such as weight lifting, dance, yoga, soccer, baseball, running, football, skiing, tennis, rehabilitation, and/or other sports or activities. This movement data includes, for instance, expected range of motion for particular movements of one or more skills of the activity, velocity for one or more of the particular movements, etc. In one example, the activity information is obtained from the web using, for instance, IBM Watson, which is a product of International Business Machines Corporation, Armonk, N.Y., and provided, retrieved or otherwise obtained by processor 110. In other examples, the activity information is stored in a database or other entity, which is accessed by, retrieved or otherwise obtained by processor 110. IBM and IBM WATSON are registered trademarks of International Business Machines Corporation, Armonk, N.Y. Other names used herein may be registered trademarks, trademarks or product names of International Business Machines Corporation or other companies.

Historical profile information 114 includes, for instance, profile information for the particular subject, which is based on, for instance, physical attributes 116 of the subject, such as weight, age, bone density, chronic illness, physical restrictions, etc. of the individual; pre-determined movement data 118 for the subject obtained from a setup phase, including, for example, natural range of motion/movement limitations for the subject, based on the activity; and/or updated movement data 106. Physical attributes 116 and/or pre-determined movement data 118 may also include external influences, such as whether the subject uses a cane, a walker, crutches, a wheelchair or other assistance device.

Alert processor 110 analyzes activity information 112 and historical profile 114 to determine whether a movement of the individual is in a danger threshold. For instance, alert processor 110 analyzes the movement data provided by the sensors and updated movement data, if any, taking into consideration movement data for the activity being performed, physical attributes of the subject and natural range of motion or limitations/restrictions of the subject to determine whether the movement of the subject is in a danger threshold. For instance, a determination is made as to whether an angle of a limb is within an acceptable range of angles, as predetermined based on, e.g., the activity, physical attributes and/or predetermined movement data. If movement of the limb is not within the range of acceptable angles, then, in one example, the danger threshold is met. Many other examples and/or variations are possible.

In one example, if the danger threshold is met, INQUIRY 120, then one or more actions are taken, including generating an alert, STEP 122. As examples, the one or more actions include generating the alert, recording the data, and/or continuing to monitor. The alert may include determining one or more possible injuries and informing the subject and/or a responder or others to the possibility of injury, STEP 124. However, if the threshold is not met, INQUIRY 120, then one or more actions, other than generating an alert, are taken, STEP 150. As examples, the one or more actions include recording the data, continuing to monitor and/or updating movement data 106. Although example actions are provided for both cases, the threshold being met/not met, other, different, fewer and/or additional actions may be taken. For instance, if the threshold is met, updated movement data and/or one or more profiles may be updated. Other variations are also possible.

Figure 1B:
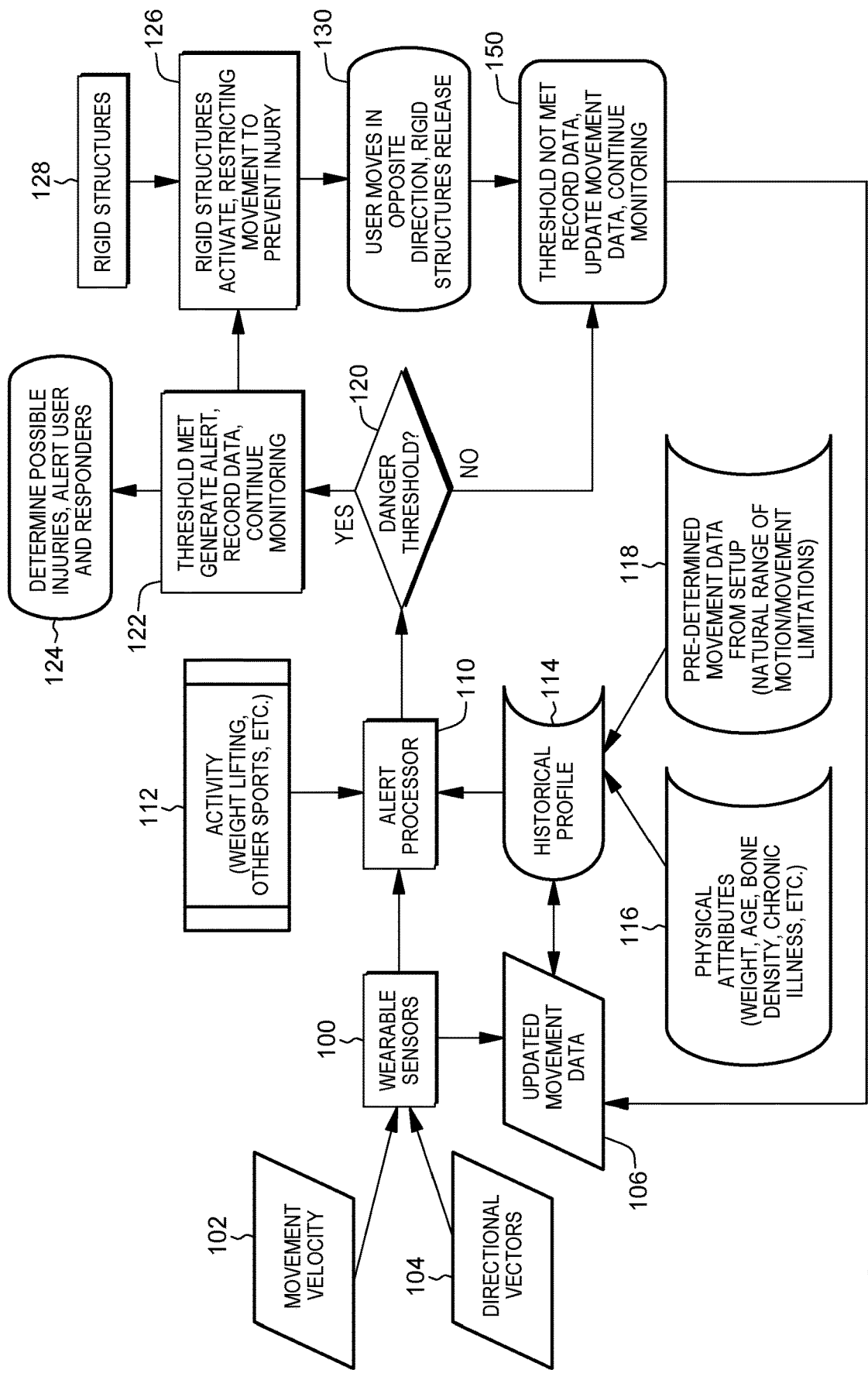
FIG. 1B depicts another example of alert processing used in accordance with one or more aspects of the present invention.

In a further aspect, based on the threshold being met, one or more physical stimuli are employed to guide the subject away from the dangerous position or to perform the intended movement correctly. As one example, referring to FIG. 1B, based on the threshold being met, STEP 122, the action further includes activating a rigid structure 128 to restrict movement to prevent the injury, STEP 126. The rigid structure is, for instance, a bag of air, memory material, etc., that is a part of or separate from the wearable apparel and used, for instance, to apply pressure to a part of the body (e.g., arm, leg, etc.) to adjust the movement, including, for instance, stopping the movement, blocking the movement, revising the movement, etc. Based on the subject moving the part of the body in another direction, such as the opposite direction, the rigid structure is released, STEP 130, and processing continues to STEP 150, in which the data is recorded, movement data is updated and/or monitoring is continued.

Figure 1C:
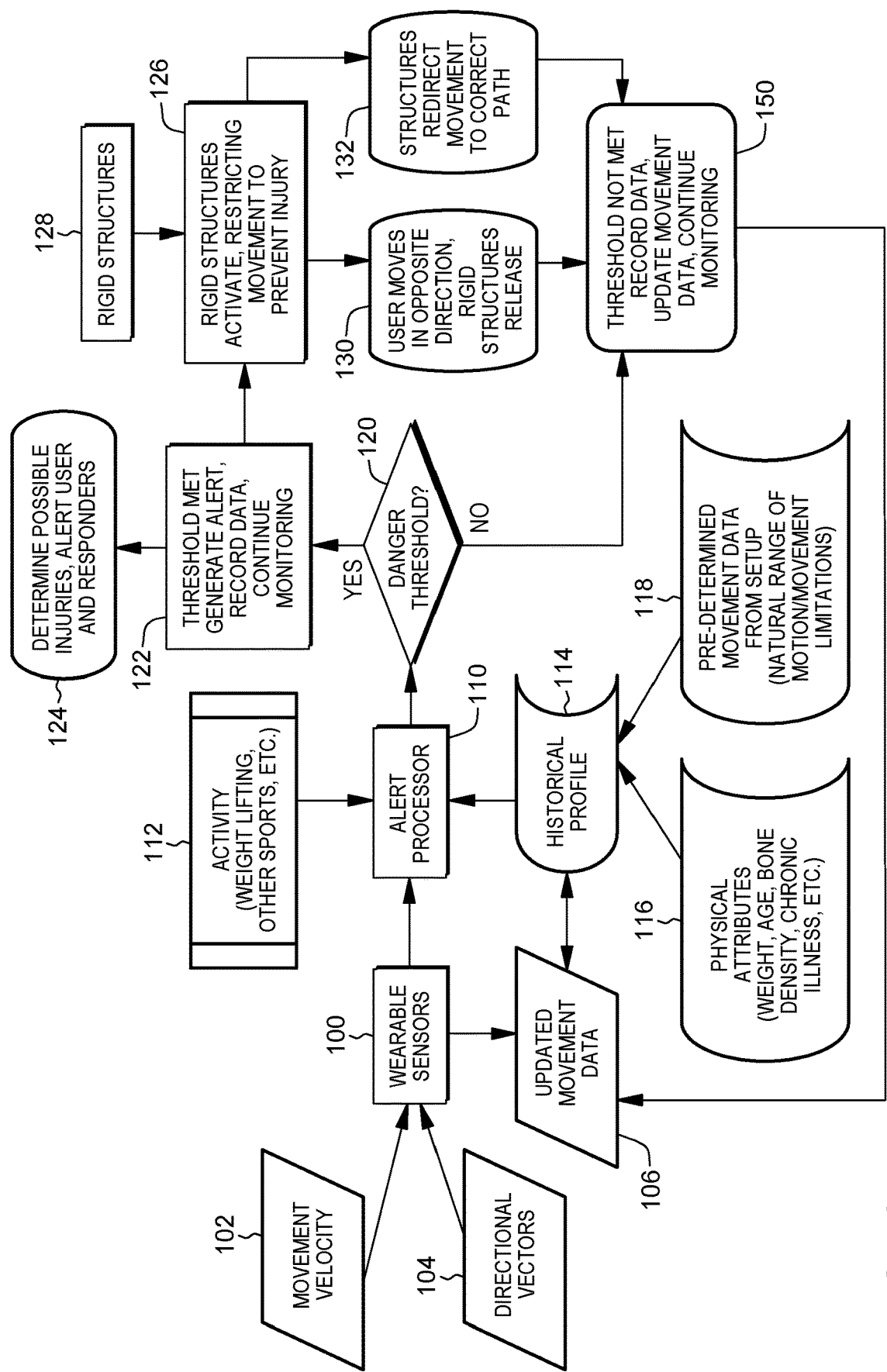
FIG. 1C depicts yet another example of alert processing used in accordance with one or more aspects of the present invention.

In yet a further aspect, referring to FIG. 1C, one or more of the rigid structures redirect movement of the subject to correct the path, STEP 132. For instance, the rigid structure puts pressure on the limb that is in the danger zone, moving the limb, even slightly, to a different position. The position is determined by the activity and data associated therewith that determines the appropriate position for the particular skill. Processing then continues with STEP 150.

In one or more aspects, different and/or additional actions may be taken. For example, STEP 124 is optional when using the rigid structures. Many other variations are possible.

As described above, one or more aspects of the present invention are used to detect and/or prevent injuries while participating in an activity. In one or more aspects, based at least in part on sensor information, a wearable apparel or other mechanism becomes rigid in certain areas such that the subject is prevented or limited from moving any further in a potentially harmful direction. The subject may move, however, in a manner that reduces the harmful risk, but not increases it. Further, if the risk factor was based on velocity of the movement, the rigidity may limit or reduce the velocity of the movement, but not limit the range of motion. Other examples and variations are also possible.

Further, in accordance with an aspect of the present invention, one or more aspects are used in skills training for selected activities. In one aspect, the subject wears the wearable apparel while performing an activity, such as weight lifting, dance, yoga, soccer, baseball, running, football, skiing, tennis, rehabilitation, etc. Then, when a skill for a selected activity is attempted, the subject's movements are monitored and compared to predefined movements for that skill to determine whether the individual has performed the skill correctly. When the skill is performed accurately, in one example, data is saved as a template for future reference. As the subject practices the skill, the current movement is compared with the subject's saved movement, and if they deviate by a selected amount, the subject is notified and/or prevented from performing the skill. Additionally, in one aspect, the movement is monitored and analyzed. If the movement detected is one that is progressing in an incorrect manner, the wearable apparel or other mechanism becomes rigid in certain areas to apply corrective measure to the movement, guiding the movement onto a correct path.

Figure 2:
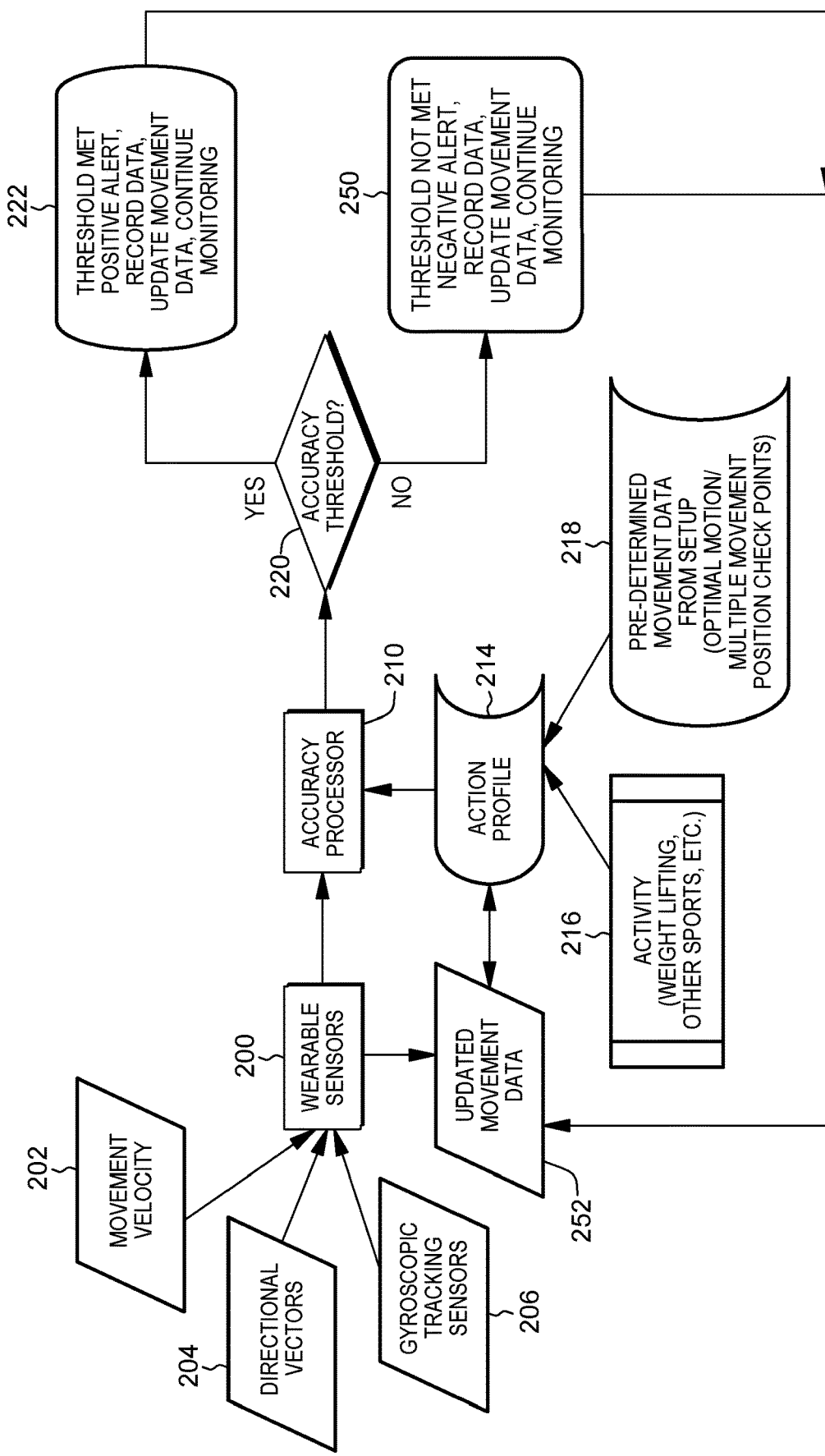
FIG. 2 depicts one example of training processing used in accordance with one or more aspects of the present invention.

Further details of using one or more aspects of the present invention in skills training are described with reference to FIG. 2. In one example, one or more sensors 200 of a wearable apparel track different statistics, including, for instance, movement velocity 202 and directional vectors 204 of various limbs or body parts, depending on placement of the sensors; and angular velocity via, e.g., gyroscopic tracking sensors 206. For instance, one or more sensors may be situated in a wearable apparel, such as, but not limited to, a brace, shirt or other apparel worn over the shoulder that monitors direction and/or velocity in movement of the shoulder in various motions, such as throwing overhand or underhand, picking up an item, weight lifting, etc. Similarly, one or more sensors may be situated in a wearable apparel, such as, but not limited to, a brace, wrap, pants or other apparel for the knee or leg that monitors direction and/or velocity in movement of the knee or leg in various motions, such as kicking, bending, lifting, etc. The sensed information is used to update movement data 252 and/or is provided as input to a processor 210. In this example, processor 210 is used in training of skills, and in particular, to facilitate correct performance of skills of an activity, and thus, is referred to herein as an accuracy processor.

Processor 210 also receives, for instance, action profile information 214. Action profile information 214 includes, for instance, activity information 216 and pre-determined movement data from setup 218. Activity information 216 includes, for instance, movement data for specific activities, such as weight lifting, dance, yoga, soccer, baseball, running, football, skiing, tennis, rehabilitation, and/or other sports or activities. This movement data includes, for instance, expected range of motion for particular movements of one or more skills of the activity, velocity for one or more of the particular movements, etc. In one example, the activity information is obtained from the web using, for instance, IBM Watson, and provided, retrieved or otherwise obtained by processor 210 (e.g., as part of action profile 214 or separately). In other examples, the activity information is stored in a database or other entity, which is accessed by, retrieved or otherwise obtained by processor 210. Pre-determined movement data from setup 218 includes, for example, optimal motion/multiple movement position check points for a subject obtained from a setup phase, including, for example, natural range of motion/movement limitations for the subject, based on the activity. The pre-determined movement data may also include external influences, such as whether the subject uses a cane, a walker, crutches, a wheelchair or other assistance device.

Accuracy processor 210 analyzes the information of action profile 214 to determine whether a movement of the individual is within an accuracy threshold, STEP 220. For instance, accuracy processor 210 analyzes the movement data provided by the sensors and updated movement data, if any, taking into consideration movement data for the activity being performed, and natural range of motion or limitations/restrictions of the subject to determine whether the movement of the subject is in an accuracy threshold. For instance, in one particular example, a determination is made as to whether an angle of an arm when throwing a ball is within a range of acceptable angles, as predetermined based on, e.g., the skill being performed for the particular activity and/or the predetermined movement data. If so, then the movement is within the accuracy threshold. Many other tests, examples, and/or variations are possible to determine whether a movement is within the accuracy threshold.

In one example, if the accuracy threshold is met, INQUIRY 220, then one or more actions are taken, including, for instance, generating a positive alert, STEP 222. As examples, the one or more actions include generating the positive alert, recording the data, updating the movement data, and/or continuing to monitor. In other examples, the positive alert is not performed. However, if the threshold is not met, INQUIRY 220, then one or more actions are taken, including, for instance, generating a negative alert, STEP 250. As examples, the one or more actions include generating the negative alert, recording the data, continuing to monitor and/or updating movement data. In either case, processing continues to STEP 252, in one example. Although example actions are provided for both cases, the threshold being met/not met, other, different, fewer and/or additional actions may be taken.

In one embodiment, there is a training progression, in which a training plan is staggered allowing the subject's skills and range of motion to increase. As the subject is able to perform a particular skill at one phase of training, the data, including, e.g., the action profile, is updated, and training proceeds to a next phase. In the next phase, what may have been considered improper or dangerous in a previous phase is no longer considered improper or dangerous.

Although various examples of activities and actions are provided herein, other activities and/or actions may be performed without departing from aspects of the present invention. Further, as indicated herein, although various types of wearable apparel are described, many other types of apparel may be used without departing from aspects of the present invention. For instance, any type of apparel that can include or be associated with sensors that can monitor a subject's movement is usable.

Figure 4A:
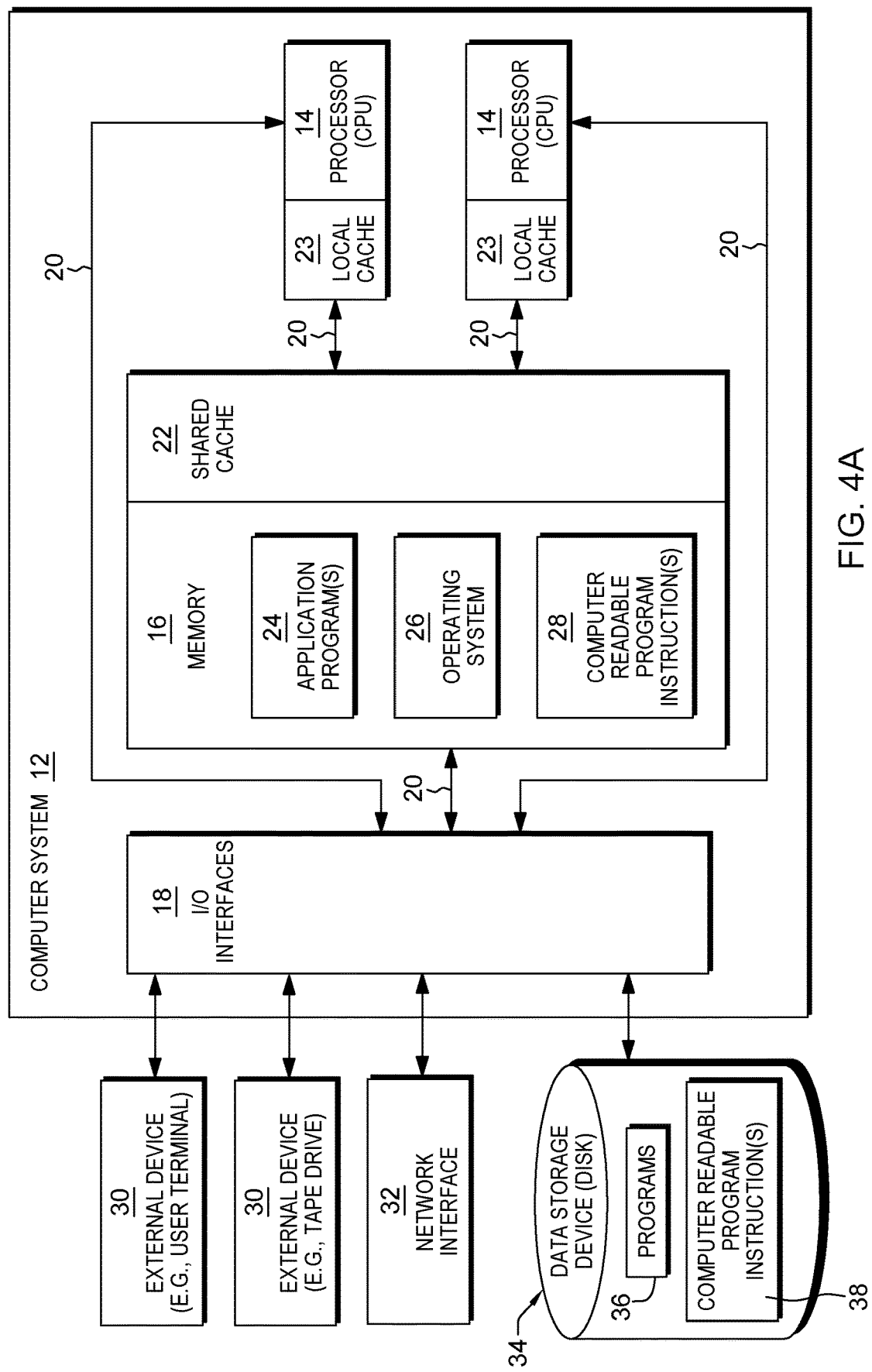
FIG. 4A depicts one example of a computing environment to incorporate and use one or more aspects of the present invention.

Further details regarding processors that may be used in one or more aspects, including an example environment that may include the processors, are described with reference to FIG. 4A. Referring to FIG. 4A, one example of a computer system that includes processors that may be used by one or more aspects of the present invention is described. In this example, the computer system is part of a computing environment including additional components that may or may not be used by aspects of the present invention.

As shown in FIG. 4A, a computing environment 10 includes, for instance, a computer system 12 shown, e.g., in the form of a general-purpose computing device. Computer system 12 may include, but is not limited to, one or more processors or processing units 14 (e.g., central processing units (CPUs)), a memory 16 (a.k.a., system memory, main memory, main storage, central storage or storage, as examples), and one or more input/output (I/O) interfaces 18, coupled to one another via one or more buses and/or other connections 20.

Bus 20 represents one or more of any of several types of bus structures, including a memory bus or memory controller, a peripheral bus, an accelerated graphics port, and a processor or local bus using any of a variety of bus architectures. By way of example, and not limitation, such architectures include the Industry Standard Architecture (ISA), the Micro Channel Architecture (MCA), the Enhanced ISA (EISA), the Video Electronics Standards Association (VESA) local bus, and the Peripheral Component Interconnect (PCI).

Memory 16 may include, for instance, a cache 22, such as a shared cache, which may be coupled to local caches 23 of processors 14. Further, memory 16 may include one or more programs or applications 24, an operating system 26, and one or more computer readable program instructions 28. Computer readable program instructions 28 may be configured to carry out functions of embodiments of aspects of the invention.

Computer system 12 may also communicate via, e.g., I/O interfaces 18 with one or more external devices 30, one or more network interfaces 32, and/or one or more data storage devices 34. Example external devices include a user terminal, a tape drive, a pointing device, a display, etc. Network interface 32 enables computer system 12 to communicate with one or more networks, such as a local area network (LAN), a general wide area network (WAN), and/or a public network (e.g., the Internet), providing communication with other computing devices or systems.

Data storage device 34 may store one or more programs 36, one or more computer readable program instructions 38, and/or data, etc. The computer readable program instructions may be configured to carry out functions of embodiments of aspects of the invention.

Computer system 12 may include and/or be coupled to removable/non-removable, volatile/non-volatile computer system storage media. For example, it may include and/or be coupled to a non-removable, non-volatile magnetic media (typically called a "hard drive"), a magnetic disk drive for reading from and writing to a removable, non-volatile magnetic disk (e.g., a "floppy disk"), and/or an optical disk drive for reading from or writing to a removable, non-volatile optical disk, such as a CD-ROM, DVD-ROM or other optical media. It should be understood that other hardware and/or software components could be used in conjunction with computer system 12. Examples, include, but are not limited to: microcode, device drivers, redundant processing units, external disk drive arrays, RAID systems, tape drives, and data archival storage systems, etc.

Computer system 12 may be operational with numerous other general purpose or special purpose computing system environments or configurations. Examples of well-known computing systems, environments, and/or configurations that may be suitable for use with computer system 12 include, but are not limited to, personal computer (PC) systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

In one example, a processor, such as processor 14, may execute one or more components to perform one or more aspects of the present invention. These components may be stored in memory, including main memory (e.g., memory 16) and/or one or more caches (e.g., shared cache 22, local cache 23) and/or external storage (e.g., device 34), and may be executed by one or more processors (e.g., processor 14). As examples, processor 14 is alert processor 110 or accuracy processor 210. Further, in one or more embodiments, alert processor 110 and accuracy processor 210 are the same processor; in other embodiments, they are different processors. Further, processor 110 and/or processor 210 may be part of a computer system, such as computer system 12, or part of a computing environment, such as computing environment 10, or may be separate therefrom. Many variations are possible.

Figure 4B:
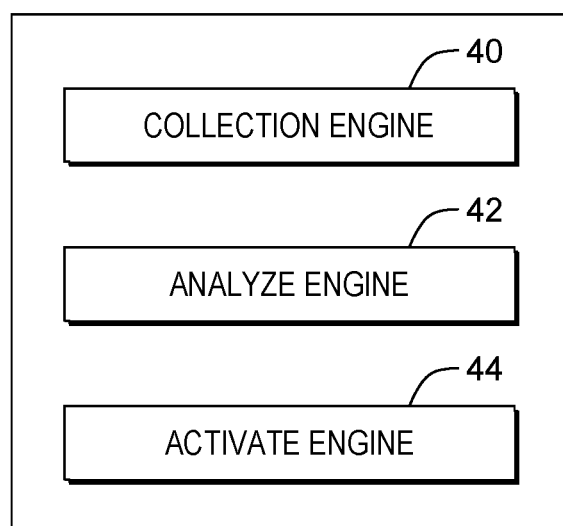
FIG. 4B depicts further details of a processor of FIG. 4A, in accordance with one or more aspects of the present invention.

In one example, referring to FIG. 4B, the components of a processor (e.g., processor 14, such as processor 110 or processor 210) to perform one or more aspects of the present invention include a collection engine 40 to collect information regarding the movements of a subject being examined (e.g., from one or more sensors), activity information, updated movement data, physical attributes, pre-determined movement data from setup and/or other data; an analyze engine 42 to analyze the collected information to determine whether a danger threshold and/or an accuracy threshold have been met; and an activate engine 44 that initiates and/or performs an action to provide notification of a potential injury or actual injury, prevent injury, and/or facilitate accurate performance of a skill in skills training. The components executed by a processor may be individual components or combined in one component. Further, there may be more, fewer and/or different components. Many variations are possible.

As described herein, there are many situations or activities in which a subject may move in such a way that can be harmful to the body. Therefore, in accordance with an aspect of the present invention, wearable technology, cognitive technology, machine learning and/or knowledge of range of motion during different individual states in performing a skill are used to create a specialized profile for an individual that is used to detect a potential injury and provide an alert notification of same. Further, if the detected movement of the individual goes beyond the normal range of the individual, such as a dislocated shoulder or ankle, an additional alert notification is generated. To collect, maintain, and analyze the information, as well as generate the alerts and/or initiate or perform an action, one or more devices are used including, but not limited to, sensors and processors.

Figure 5:
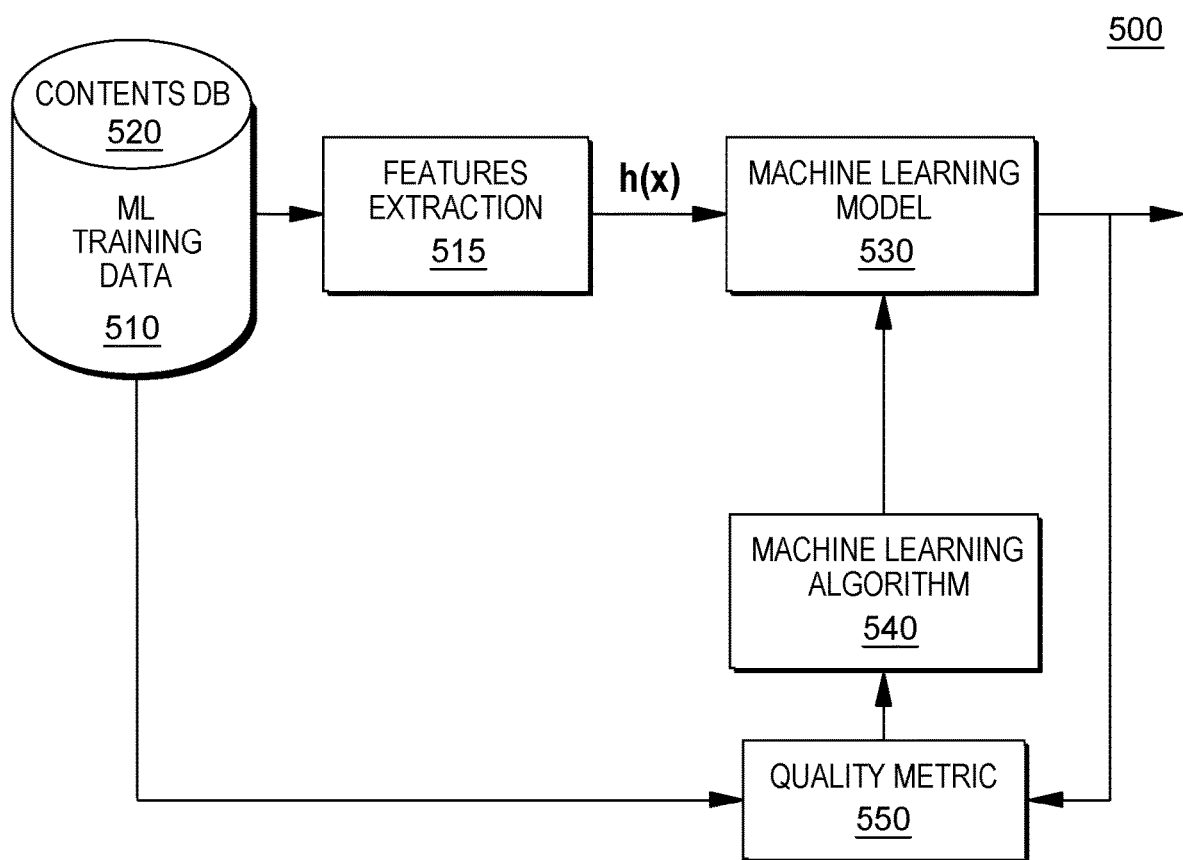
FIG. 5 depicts one example of using machine learning in one or more aspects of the present invention.

As an example, machine learning is used to detect and/or prevent injury and/or to facilitate performance of skills training. Machine learning algorithms generate and train algorithms to create a model utilized to detect and/or prevent injury of a given subject or to be used in skills training. For instance, in an initialization stage, program code (e.g., hardware and/or software) trains these algorithms, based on patterns for a given subject (and/or across all subjects with certain shared attributes). FIG. 5 is an example of a machine learning training system 500 utilized, in one or more aspects, to perform cognitive analyses of various inputs, including sensed data (e.g., movement velocity 102, directional vectors 104 and/or gyroscopic tracking data), movement data (e.g., updated movement data 106 or 252), historical data (e.g., historical profile 114), action data (e.g., action profile 214) and/or other data. Training data utilized to train the model in one or more embodiments of the present invention includes, for instance, data that is personalized to the subject, including but not limited to, age, health, range of motion, etc. The program code in embodiments of the present invention performs a cognitive analysis to generate data structures, including algorithms utilized by the program code to predict states of a given subject. Machine learning (ML) solves problems that are not solved with numerical means alone. In this ML-based example, program code extracts various features/attributes from ML training data 510 (e.g., historical data collected from various data sources relevant to the subject), which may be resident in one or more databases 520 comprising subject-related data and general data. Features 515 are utilized to develop a predictor function, h(x), also referred to as a hypothesis, which the program code utilizes as a machine learning model 530.

In identifying various subject states and/or behaviors indicative of states in the ML training data 510, the program code can utilize various techniques including, but not limited to, mutual information, which is an example of a technique that can be utilized to identify features in an embodiment of the present invention. Further embodiments of the present invention utilize varying techniques to select features (elements, patterns, attributes, etc.), including but not limited to, diffusion mapping, principal component analysis, recursive feature elimination (a brute force approach to selecting features), and/or a Random Forest, to select the attributes related to various subject states. The program code may utilize a machine learning algorithm 540 to train the machine learning model 530 (e.g., the algorithms utilized by the program code), including providing weights for the conclusions, so that the program code can train the predictor functions that comprise the machine learning model 530. The conclusions may be evaluated by a quality metric 550. By selecting a diverse set of ML training data 510, the program code trains the machine learning model 530 to identify and weight various attributes (e.g., features, patterns) that correlate to various states of a subject.

The model generated by the program code is self-learning as the program code updates the model based on active subject feedback received from subjects, as well as from the feedback received from the sensor data, related to monitoring the subject. For example, when the program code determines that there is a potential injury at a given time that was not previously predicted by the model, the program code alerts the subject, but also, utilizes a learning agent to update the model to reflect the state of the subject, in order to improve predictions in the future. Additionally, when the program code determines that a prediction is incorrect, either based on receiving user feedback through an interface or based on continuously monitoring the subject, the program code updates the model to reflect the inaccuracy of the prediction for the given period of time. Program code comprising a learning agent cognitively analyzes the data deviating from the modeled expectations and adjusts the model in order to increase the accuracy of the model, moving forward.

In one or more embodiments, program code executing on one or more processors, utilizes an existing cognitive analysis tool or agent to tune the model, based on data obtained from the various data sources, including sensor data. One or more embodiments utilize IBM Watson as the cognitive agent. In one or more embodiments, the program code interfaces with IBM Watson application programming interfaces (APIs) to perform a cognitive analysis of obtained data.

In one or more embodiments, the program code trains aspects of the IBM Watson Application Program Interface (API) to learn the relationships between physiological elements from the sensors and the patterns of the subject. Utilizing an existing cognitive agent, such as IBM Watson expands the type of subject data that the program code can integrate into the model. For example, sensor data can include documentary, visual, and audio data, which the program code can process, based on its utilization of IBM Watson. Specifically, in one or more embodiments, certain of the APIs of the IBM Watson API comprise a cognitive agent (e.g., learning agent) that includes one or more programs, including, but not limited to, natural language classifiers, Retrieve and Rank (i.e., a service available through the IBM Watson Developer Cloud that can surface the most relevant information from a collection of documents), concepts/visual insights, trade off analytics, document conversion, and/or relationship extraction. In an embodiment, one or more programs analyze the data obtained by the program code across various sources utilizing one or more of a natural language classifier, retrieve and rank APIs, and trade off analytics APIs. The IBM Watson Application Program Interface (API) can also provide audio related API services, in the event that the collected data includes audio, which can be utilized by the program code, including but not limited to natural language processing, text to speech capabilities, and/or translation.

In generating and updating the model, the program code can segment future periods into distinct portions, in order to provide users with a usable guide for anticipating the state of a subject. In one or more embodiments, the program code divides each twenty-four (24) hour period into defined time segments of a certain length (e.g., twenty (20) minutes). The program code can generate an average state prediction for each distinct period, for example, by synthesizing or averaging the data (e.g., sensor data) over each time segment.

The program code can provide state predictions and/or alerts for a given subject as varying values. In one or more embodiments, the program code calculates a binary injury value for the subject, which the program code provides to users (e.g., subscribers). Thus, in one or more embodiments, the program code indicates to a user whether an injury is predicted for a given subject. As discussed above, in one or more embodiments, should the subject behavior deviate from the model predictions, based on continuously monitoring the subject (e.g., utilizing IoT devices and other computing devices including environmental and/or personal sensors), the program code can immediately alert users, for example, when a potential injury is detected. Whether users receive these immediate alerts may depend upon a location of the user.

In one or more embodiments, the program code utilizes a neural network to analyze subject-related data to generate the model utilized to predict the state of a given subject at a given time. Neural networks are a biologically-inspired programming paradigm which enable a computer to learn from observational data, in this case, sensor data, and/or other data. This learning is referred to as deep learning, which is a set of techniques for learning in neural networks. Neural networks, including modular neural networks, are capable of pattern (e.g., state) recognition with speed, accuracy, and efficiency, in situations where data sets are multiple and expansive, including across a distributed network, including but not limited to, cloud computing systems. Modern neural networks are non-linear statistical data modeling tools. They are usually used to model complex relationships between inputs and outputs or to identify patterns (e.g., states) in data (i.e., neural networks are non-linear statistical data modeling or decision making tools). In general, program code utilizing neural networks can model complex relationships between inputs and outputs and identify patterns in data. Because of the speed and efficiency of neural networks, especially when parsing multiple complex data sets, neural networks and deep learning provide solutions to many problems in multiple source processing, which the program code in one or more embodiments accomplishes when obtaining data and generating a model for predicting states of a given subject during particular intervals (e.g., during particular movements).

One or more embodiments may utilize a neural network (NN) to predict future states of a given subject. Utilizing the neural network, the program code can predict the likelihood of the subject being in a given state at a subsequent time. The program code obtains (or derives) data related to the subject from various sources to generate an array of values (possible states) to input into input neurons of the NN. Responsive to these inputs, the output neurons of the NN produce an array that includes the predicted states. The program code can automatically transmit notifications related to the predicted states based on the perceived validity.

In one or more embodiments, a neuromorphic processor or trained neuromorphic chip can be incorporated into the computing resources executing the program code. One example of a trained neuromorphic chip that is utilized in an embodiment of the present invention is the IBM TrueNorth chip, produced by International Business Machines Corporation.

The IBM TrueNorth chip, also referred to as TrueNorth, is a neuromorphic complementary metal-oxide-semiconductor (CMOS) chip. TrueNorth includes a manycore network on a chip design (e.g., 4096 cores), each one simulating programmable silicon "neurons" (e.g., 256 programs) for a total of just over a million neurons. In turn, each neuron has 256 programmable synapses that convey the signals between them. Hence, the total number of programmable synapses is just over 268 million ($2^{28}$). Memory, computation, and communication are handled in each of the 4096 neurosynaptic cores, so TrueNorth circumvents the von-Neumann-architecture bottlenecks and is very energy-efficient.

One or more aspects of the present invention are inextricably tied to computing and improve the technical fields of injury detection, injury prevention, skills training and/or machine learning, as examples. Technological improvements are provided in automatically detecting a potential injury and preventing such an injury to improve safety. Further, technological improvements are provided in automatically making an adjustment for skills training.

In one embodiment, wearable apparel is provided that includes sensors used to learn the range of motion of a subject, including, for instance, the direction, velocity and/or angular velocity of limbs, head and torso, when the subject is wearing the apparel and performing a skill as part of an activity. The learned information is stored in a profile specific for the subject. As the subject performs one or more skills, the subject's profile is monitored to determine whether the subject is exceeding range of motion limitations defined for the subject. If so, an alert of possible injury is provided.

Further, in one aspect, the wearable apparel may become rigid to prevent a potentially harmful movement. A user profile is stored for each individual activity. Additionally, the subject's movements while performing one or more skills of the activity are monitored and recorded. This is compared, in one example, with a stored template of correctly performed movements, allowing the subject to compare progress against the template.

Although many examples and embodiments are provided herein, other variations and embodiments are possible.

One or more aspects may relate to cloud computing.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
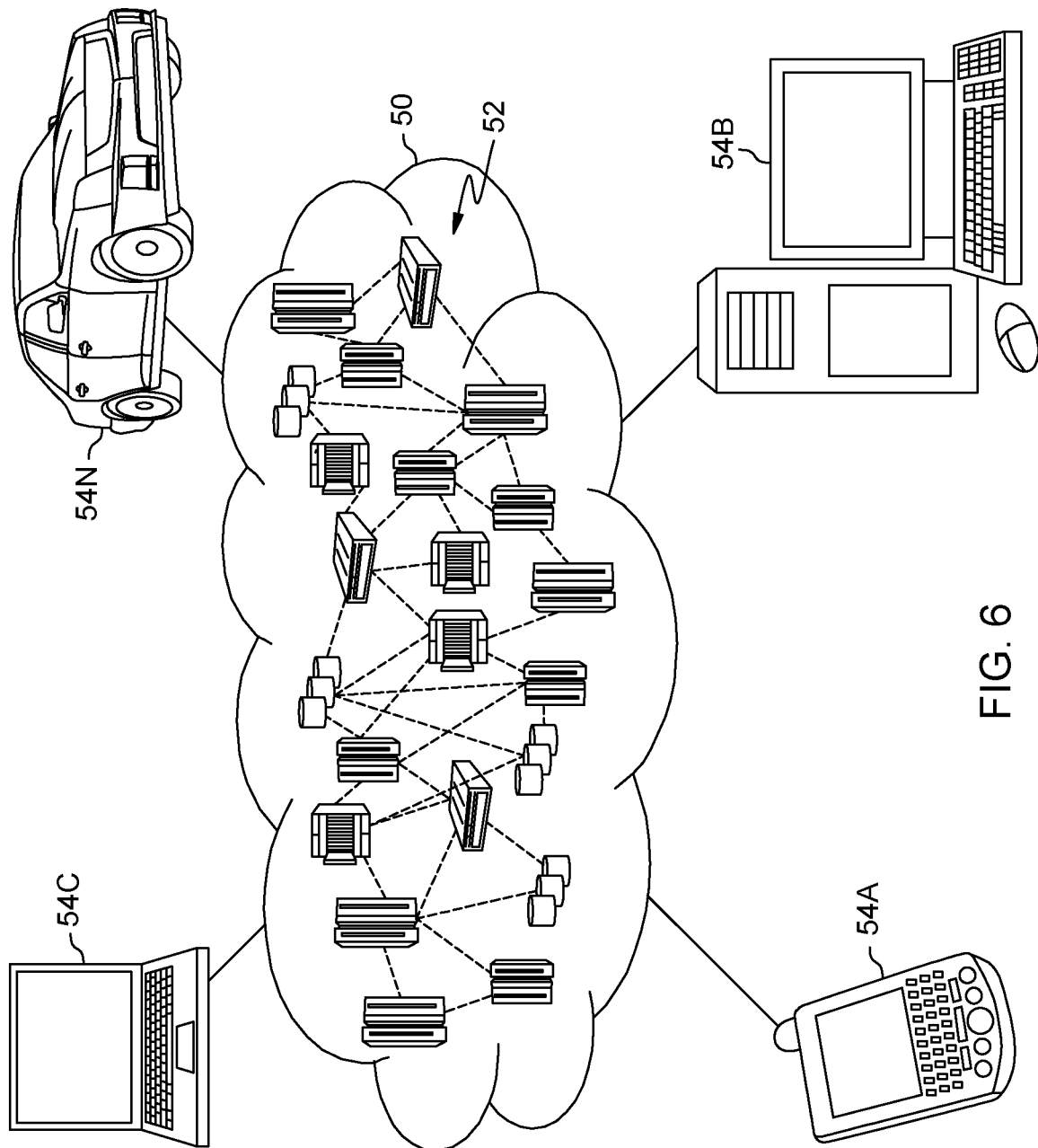
FIG. 6 depicts one embodiment of a cloud computing environment.

Referring now to FIG. 6, illustrative cloud computing environment 50 is depicted. As shown, cloud computing environment 50 comprises one or more cloud computing nodes 52 with which local computing devices used by cloud consumers, such as, for example, personal digital assistant (PDA) or cellular telephone 54A, desktop computer 54B, laptop computer 54C, and/or automobile computer system 54N may communicate. Nodes 52 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 52 and cloud computing environment 50 can communicate with any type of computerized device over any type of network and/or network addressable connection (e.g., using a web browser).

Figure 7:
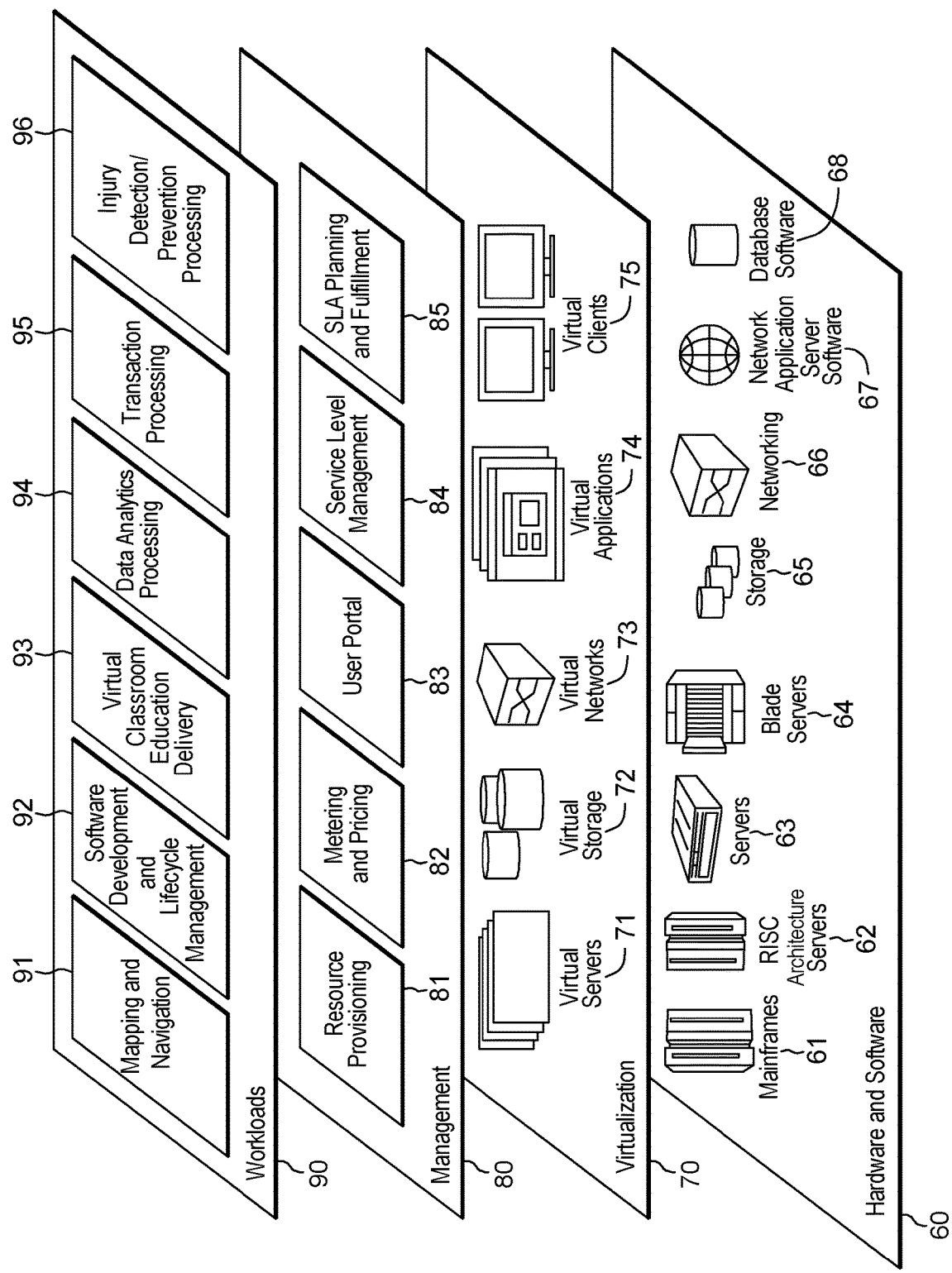
FIG. 7 depicts one example of abstraction model layers.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides idsubject verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and injury detection/prevention processing 96.

Aspects of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In addition to the above, one or more aspects may be provided, offered, deployed, managed, serviced, etc. by a service provider who offers management of customer environments. For instance, the service provider can create, maintain, support, etc. computer code and/or a computer infrastructure that performs one or more aspects for one or more customers. In return, the service provider may receive payment from the customer under a subscription and/or fee agreement, as examples. Additionally or alternatively, the service provider may receive payment from the sale of advertising content to one or more third parties.

In one aspect, an application may be deployed for performing one or more embodiments. As one example, the deploying of an application comprises providing computer infrastructure operable to perform one or more embodiments.

As a further aspect, a computing infrastructure may be deployed comprising integrating computer readable code into a computing system, in which the code in combination with the computing system is capable of performing one or more embodiments.

As yet a further aspect, a process for integrating computing infrastructure comprising integrating computer readable code into a computer system may be provided. The computer system comprises a computer readable medium, in which the computer medium comprises one or more embodiments. The code in combination with the computer system is capable of performing one or more embodiments.

Although various embodiments are described above, these are only examples. For example, other types of devices, sensors and/or tracking components, etc. may be used in one or more embodiments. Many variations are possible.

Further, other types of computing environments can benefit and be used. As an example, a data processing system suitable for storing and/or executing program code is usable that includes at least two processors coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A method of facilitating prevention of injuries, the method comprising:
   receiving input activity information, the input activity information comprising expected movement data for a particular sport activity being performed by a subject, the expected movement data comprising expected range of motion for particular movements of one or more skills of the sport activity, and velocity for one or more of the particular movements;
   obtaining, via a processor, data regarding a movement being performed by the subject during the sport activity, the data being obtained from wearable apparel worn by the subject during the sport activity, the wearable apparel having multiple sensors, the multiple sensors facilitating tracking movement velocity and one or more directional vectors of one or more parts of the subject during the sport activity;
   automatically detecting, based on the input activity information and at least in part on the data obtained by the wearable apparel during the sport activity, that the movement has a potential of causing injury to the subject; and
   initiating application of one or more physical stimuli during the sport activity, based on automatically detecting that the movement has the potential of causing injury to the subject, to cause the subject to adjust the movement to prevent the injury during the sport activity.

2. The method of claim 1, wherein the initiating application of the one or more physical stimuli guide the subject to perform the movement correctly.

3. The method of claim 1, further comprising:
   storing an action profile for the sport activity that is tailored to the subject; and
   using the action profile in the automatically detecting that the movement has the potential of causing injury to the subject.

4. The method of claim 3, wherein the action profile is based on one or more attributes of the subject and includes one or more characteristics of the sport activity, wherein at least one attribute of the subject and at least one characteristic of the sport activity are used to determine whether the movement has the potential of causing injury to the subject.

5. The method of claim 1, further comprising:
gathering predefined data regarding the sport activity, the predefined data including information regarding proper technique for performing one or more skills of the sport activity; and
using the predefined data to train the subject in correct movement for the sport activity.

6. The method of claim 1, wherein the automatically detecting comprises using a training plan to determine whether the movement has the potential of causing injury, wherein the training plan for the sport activity includes a plurality of training progressions and the potential of causing injury is based on which training progression of the training plan is active.

7. The method of claim 1, wherein the obtaining data regarding the movement being performed by the subject during the sport activity includes obtaining data from a plurality of wearable apparel, the plurality of wearable apparel covering a plurality of parts of the subject.

8. The method of claim 1, further comprising:
determining that the subject has correctly performed a skill of the sport activity; and
storing a template of the correctly performed skill for the subject, based on determining that the subject has correctly performed the skill, the template to be used in skills training for the sport activity.

9. A system for facilitating prevention of injuries, the system comprising:
a memory; and
a processor coupled to the memory, the processor configured to perform a method, the method comprising:
receiving input activity information, the input activity information comprising expected movement data for a particular sport activity being performed by a subject, the expected movement data comprising expected range of motion for particular movements of one or more skills of the sport activity, and velocity for one or more of the particular movements;
obtaining, via a processor, data regarding a movement being performed by the subject during the sport activity, the data being obtained from wearable apparel worn by the subject during the sport activity, the wearable apparel having multiple sensors, the multiple sensors facilitating tracking movement velocity and one or more directional vectors of one or more parts of the subject during the sport activity;
automatically detecting, based on the input activity information and at least in part on the data obtained by the wearable apparel during the sport activity, that the movement has a potential of causing injury to the subject; and
initiating application of one or more physical stimuli during the sport activity, based on automatically detecting that the movement has the potential of causing injury to the subject, to cause the subject to adjust the movement to prevent the injury during the sport activity.

10. The system of claim 9, wherein the method further comprises:
storing an action profile for the sport activity that is tailored to the subject; and
using the action profile in the automatically detecting that the movement has the potential of causing injury to the subject.

11. The system of claim 9, wherein the method further comprises:
gathering predefined data regarding the sport activity, the predefined data including information regarding proper technique for performing one or more skills of the sport activity; and
using the predefined data to train the subject in correct movement for the sport activity.

12. The system of claim 9, wherein the automatically detecting comprises using a training plan for the sport activity to determine whether the movement has the potential of causing injury, wherein the training plan includes a plurality of training progressions and the potential of causing injury is based on which training progression of the training plan is active.

13. The system of claim 9, wherein the method further comprises:
determining that the subject has correctly performed a skill of the sport activity; and
storing a template of the correctly performed skill for the subject, based on determining that the subject has correctly performed the skill, the template to be used in skills training for the sport activity.

14. A computer program product for facilitating prevention of injuries, the computer program product comprising:
at least one computer readable storage medium readable by a processing circuit and storing instructions for performing a method comprising:
receiving input activity information, the input activity information comprising expected movement data for a particular sport activity being performed by a subject, the expected movement data comprising expected range of motion for particular movements of one or more skills of the sport activity, and velocity for one or more of the particular movements;
obtaining, via a processor, data regarding a movement being performed by the subject during the sport activity, the data being obtained from wearable apparel worn by the subject during the sport activity, the wearable apparel having multiple sensors, the multiple sensors facilitating tracking movement velocity and one or more directional vectors of one or more parts of the subject during the sport activity;
automatically detecting, based on the input activity information and at least in part on the data obtained by the wearable apparel during the sport activity, that the movement has a potential of causing injury to the subject; and
initiating application of one or more physical stimuli during the sport activity, based on automatically detecting that the movement has the potential of causing injury to the subject, to cause the subject to adjust the movement to prevent the injury during the sport activity.

15. The computer program product of claim 14, wherein the method further comprises:
storing an action profile for the sport activity that is tailored to the subject; and
using the action profile in the automatically detecting that the movement has the potential of causing injury to the subject.

16. The computer program product of claim 14, wherein the method further comprises:
   gathering predefined data regarding the sport activity, the predefined data including information regarding proper technique for performing one or more skills of the sport activity; and
   using the predefined data to train the subject in correct movement for the sport activity.

17. The computer program product of claim 14, wherein the automatically detecting comprises using a training plan for the sport activity to determine whether the movement has the potential of causing injury, wherein the training plan includes a plurality of training progressions and the potential of causing injury is based on which training progression of the training plan is active.

18. The computer program product of claim 14, wherein the method further comprises:
   determining that the subject has correctly performed a skill of the sport activity; and
   storing a template of the correctly performed skill for the subject, based on determining that the subject has correctly performed the skill, the template to be used in skills training for the sport activity.

* * * * *